US010927175B2

(12) United States Patent
Lai et al.

(10) Patent No.: US 10,927,175 B2
(45) Date of Patent: Feb. 23, 2021

(54) METHOD FOR TREATING CANCER

(71) Applicant: Sun Jet Biotechnology Inc., Taipei (TW)

(72) Inventors: Hung-Chih Lai, Taipei (TW); Yeou-Guang Tsay, Taipei (TW)

(73) Assignee: SUN JET BIOTECHNOLOGY INC., Taipei (TW)

( * ) Notice: Subject to any disclaimer, the term of this patent is extended or adjusted under 35 U.S.C. 154(b) by 243 days.

(21) Appl. No.: 16/053,234

(22) Filed: Aug. 2, 2018

(65) Prior Publication Data
US 2019/0048081 A1 Feb. 14, 2019

Related U.S. Application Data

(60) Provisional application No. 62/542,432, filed on Aug. 8, 2017.

(51) Int. Cl.
| | |
|---|---|
| *C07K 16/28* | (2006.01) |
| *A61K 39/395* | (2006.01) |
| *A61K 33/24* | (2019.01) |
| *C07K 16/22* | (2006.01) |
| *A61P 35/00* | (2006.01) |
| *A61K 31/7068* | (2006.01) |
| *A61K 39/00* | (2006.01) |

(52) U.S. Cl.
CPC ...... *C07K 16/2818* (2013.01); *A61K 31/7068* (2013.01); *A61K 33/24* (2013.01); *A61K 39/3955* (2013.01); *A61K 39/39541* (2013.01); *A61P 35/00* (2018.01); *C07K 16/22* (2013.01); *A61K 2039/505* (2013.01); *A61K 2039/507* (2013.01); *A61K 2039/545* (2013.01)

(58) Field of Classification Search
None
See application file for complete search history.

(56) References Cited

U.S. PATENT DOCUMENTS

2017/0158776 A1* 6/2017 Feltquate .............. A61K 33/24

OTHER PUBLICATIONS https://en.wikipedia.org/wiki/PD-1_and_PD-L1_inhibitors, downloaded May 26, 2020 (Year: 2020).*
On the Horizon: Immuno-Oncology (I-O) Combinations, https://www.fda.gov/media/110075/download, downloaded May 26, 2020 (Year: 2017).*
Chen et al., Nature, Jan. 18, 2017;541(7637):321-330 (Year: 2017).*
Phase 2 Study of Pembrolizumab in Combination With Gemcitabine and Cisplatin as Neoadjuvant Therapy, at https://clinicaltrials.gov/ct2/show/NCT02690558, first posted Feb. 24, 2016, downloaded May 26, 2020 (Year: 2016).*

* cited by examiner

*Primary Examiner* — Karl J Puttlitz
(74) *Attorney, Agent, or Firm* — Birch, Stewart, Kolasch & Birch, LLP

(57) ABSTRACT

Provided is a method for treating a cancer in a subject in need thereof. The method comprises administering to the subject an anti-PD-1 agent in combination with one or more anticancer agents.

4 Claims, 1 Drawing Sheet
(1 of 1 Drawing Sheet(s) Filed in Color)

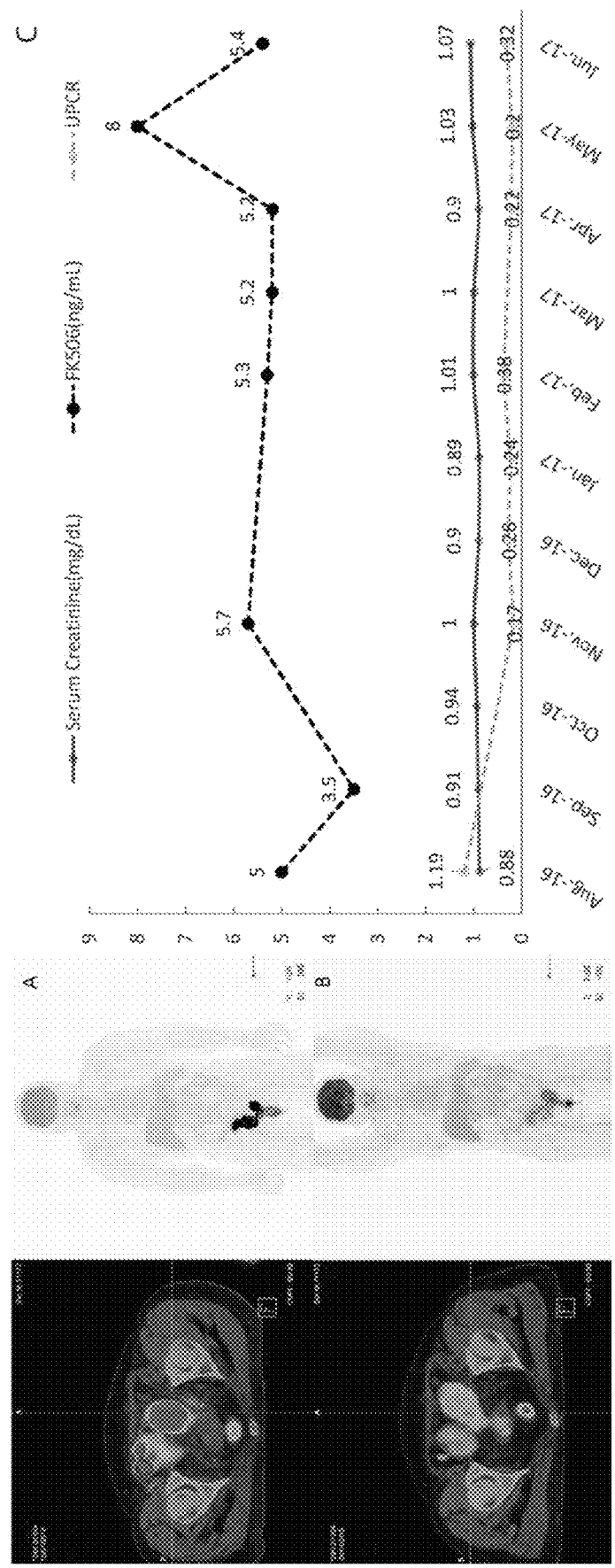

METHOD FOR TREATING CANCER

CROSS REFERENCE TO RELATED APPLICATION

This non-provisional application claims the benefit under 35 U.S.C. § 119(e) to U.S. Provisional Application No. 62/542,432, filed on Aug. 8, 2017, all of which are hereby expressly incorporated by reference into the present application.

FIELD OF THE INVENTION

The present invention pertains to a method for treating cancer.

BACKGROUND OF THE INVENTION

Antibodies targeting the programmed cell death 1 (PD)-1 receptor and its ligands have shown anti-tumor activity in multiple tumor types, including urothelial carcinoma (UC) [1]. Reports of the efficacy and safety of these antibodies in organ transplant patients are limited for risk of graft rejection.

BRIEF SUMMARY OF THE INVENTION

The present invention provides a method for treating cancer in a subject in need thereof, comprising administering to the subject an anti-PD-1 agent in combination with one or more anticancer agents.

In certain embodiments of the present invention, the anti-PD-1 agent is an anti-PD-1 antibody. In one embodiment, the anti-PD-1 antibody is pembrolizumab.

In certain embodiments of the present invention, the one or more anticancer agents include bevacizumab, cisplatin, and gemcitabine.

According to certain embodiments of the present invention, each of the anti-PD-1 agent and the one or more anticancer agents is administered in an amount which produces a synergistic effect in treating the cancer.

In certain embodiments of the present invention, the cancer is urothelial carcinoma.

In certain embodiments of the present invention, the subject bears an allograft. According to certain preferred embodiments, each of the anti-PD-1 agent and the one or more anticancer agents is administered in an amount which does not cause an allograft rejection.

It is to be understood that both the foregoing general description and the following detailed description are exemplary and explanatory only and are not restrictive of the invention.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee. The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1 shows positron emission tomography-computed tomography images before and after therapy and serum creatinine, tacrolimus (FK506) levels and urine protein to creatinine ratio over time. (A) Prior to initiation of therapy, hypermetabolism in the transplanted renal pelvis, urinary bladder, uterine cervix, and vagina. (B) 3 months following treatment, significant resolution of the hypermetabolism. (C) stable serum creatinine, tacrolimus (FK506) level and urine protein to creatinine ratio.

DETAILED DESCRIPTION OF THE INVENTION

The present invention provides a method for treating cancer in a subject in need thereof, comprising administering to the subject an anti-PD-1 agent in combination with one or more anticancer agents.

In certain embodiments of the present invention, the anti-PD-1 agent is an anti-PD-1 antibody. In one embodiment, the anti-PD-1 antibody is pembrolizumab.

In certain embodiments of the present invention, the one or more anticancer agents include bevacizumab, cisplatin, and gemcitabine.

According to certain embodiments of the present invention, each of the anti-PD-1 agent and the one or more anticancer agents is administered in an amount which produces a synergistic effect in treating the cancer.

In certain embodiments of the present invention, the cancer is urothelial carcinoma.

In certain embodiments of the present invention, the subject bears an allograft. According to certain preferred embodiments, each of the anti-PD-1 agent and the one or more anticancer agents is administered in an amount which does not cause an allograft rejection.

The present invention is further illustrated by the following examples, which are provided for the purpose of demonstration rather than limitation.

EXAMPLES

Example 1: Tumor Regression and Preservation of Graft Function after Combination with Anti-PD-1 Immunotherapy without Immunosuppressant Titration A 61-year-old woman with end-stage renal disease underwent deceased donor kidney transplantation in April 2008. Her medical history was significant for diabetes mellitus and hypertension. After transplantation, her graft remained stable on immunosuppressants with prednisolone, tacrolimus, and mycophenolate mofetil. The prednisolone was discontinued in June 2009.

She was diagnosed with UC in the left lower one-third of the ureter after a left nephroureterectomy and bladder cuff excision in May 2013. Between September 2013 and March 2016 she underwent repeated transurethral resections of the bladder tumor, and intravesical instillation with pharmarubicin, mitomycin C, and bacillus Calmette-Guerin for recurrent bladder cancer. In July 2016, she noted dysuria and vaginal spotting. A positron emission tomography-computed tomography (PET-CT) scan and cervical biopsy revealed recurrent UC invading the transplanted renal pelvis, urinary bladder, uterine cervix, and vagina (FIG. 1, (A)).

An anti-PD-1 monoclonal antibody (pembrolizumab [1 mg/kg]), and anti-cancer agents (bevacizumab [4 mg/kg], cisplatin [50 mg/m$^2$], and gemcitabine [500 mg/m$^2$]) were administered intravenously in August 2016. After four cycles of therapy, a PET-CT scan in October 2016 demonstrated significant tumor regression (FIG. 1, (B)). A sustained good partial response after 11 cycles of therapy was confirmed by a PET-CT scan in March 2017. After anti-PD-1 immunotherapy, graft function remained stable with a fixed dose of mycophenolate mofetil (1 g/day) and mild increase of tarcolimus from 9 to 10 g/day to maintain serum tacrolimus level between 5 and 10 ng/mL (FIG. 1, (C)). A mild immune-related skin maculopapular rash occurred, but resolved completely with anti-histamines.

Activation of immune cells by checkpoint inhibitors against malignant cells and cells expressing foreign antigen, such as an allograft, has been associated with cell- and antibody-mediated rejection [2, 3]. Allograft rejection after administration of anti-PD-1 agents has been widely reported in the current literature, with the exception of a renal transplant patient with metastatic duodenal adenocarcinoma. The allograft was preserved and the tumor regressed by gradually decreasing prednisolone and replacing tacrolimus with sirolimus after nivolumab [4]. In our patient, combined anti-PD-1 and anti-cancer agents successfully preserved the allograft and decreased the tumor burden without titration of immunosuppressants. Emerging data have demonstrated chemotherapy could enhance anti-tumor effects of immunotherapy by eliminations of immunosuppressive cells such as myeloid derived suppressor cells or regulatory T-cells with the use of gemcitabine or platinum-based drugs [5]. Moreover, anti-angiogenic agents could improve endogenous immune anti-tumor responses by normalization of the tumor neovasculature [5]. Thus, combined anti-PD-1 and anti-cancer agents possibly gave rise to a good treatment response and did not increase immune-related graft rejection.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES

1. Bellmunt J, de Wit R, Vaughn D J et al. Pembrolizumab as Second-Line Therapy for Advanced Urothelial Carcinoma. N Engl J Med 2017; 376: 1015-1026.
2. Lipson E J, Bagnasco S M, Moore J, Jr. et al. Tumor Regression and Allograft Rejection after Administration of Anti-PD-1. N Engl J Med 2016; 374: 896-898.
3. Boils C L, Aljadir D N, Cantafio A W. Use of the PD-1 Pathway Inhibitor Nivolumab in a Renal Transplant Patient With Malignancy. Am J Transplant 2016; 16: 2496-2497.
4. Barnett R, Barta V S, Jhaveri K D. Preserved Renal-Allograft Function and the PD-1 Pathway Inhibitor Nivolumab. N Engl J Med 2017; 376: 191-192.
5. Apetoh L, Ladoire S, Coukos G, Ghiringhelli F. Combining immunotherapy and anticancer agents: the right path to achieve cancer cure? Ann Oncol 2015; 26: 1813-1823.

What is claimed is:

1. A method for treating a cancer in a subject in need thereof, comprising
administering to the subject an anti-PD-1 agent in combination with anticancer agents, wherein each of the anti-PD-1 agent and the anticancer agents is administered in an amount which is not effective to treat the cancer when administered alone, to provide an unexpected synergistic effect in treating the cancer, wherein the anti-PD-1 agent is pembrolizumab and the dose thereof is 1 mg/kg; wherein the anticancer agents are the combination of bevacizumab, cisplatin, and gemcitabine; and wherein the dose of bevacizumab is 4 mg/kg, the dose of cisplatin is 50 mg/m$^2$, and the dose of gemcitabine 500 mg/m$^2$.

2. The method of claim 1, wherein the cancer is urothelial carcinoma.

3. The method of claim 1, wherein the subject bears an allograft.

4. The method of claim 3, wherein each of the anti-PD-1 agent and the anticancer agents is administered in an amount which does not cause an allograft rejection.

* * * * *